United States Patent
Hannula et al.

(10) Patent No.: US 7,047,056 B2
(45) Date of Patent: May 16, 2006

(54) HAT-BASED OXIMETER SENSOR

(75) Inventors: Don Hannula, San Luis Obispo, CA (US); Paul Mannheimer, Danville, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 117 days.

(21) Appl. No.: 10/606,668

(22) Filed: Jun. 25, 2003

(65) Prior Publication Data
US 2004/0267104 A1 Dec. 30, 2004

(51) Int. Cl.
*A61B 5/00* (2006.01)

(52) U.S. Cl. .................. 600/340; 600/344

(58) Field of Classification Search ........... 600/310, 600/322, 323, 340, 344
See application file for complete search history.

(56) References Cited

U.S. PATENT DOCUMENTS

| | | | |
|---|---|---|---|
| 4,321,930 A * | 3/1982 | Jobsis et al. ............ | 600/344 |
| 4,930,888 A | 6/1990 | Feisleben et al. | |
| 5,054,488 A | 10/1991 | Muz | |
| 5,217,013 A * | 6/1993 | Lewis et al. ............ | 600/342 |
| 5,246,003 A * | 9/1993 | DeLonzor ................ | 600/344 |
| 5,413,099 A | 5/1995 | Schmidt et al. | |
| 5,431,170 A * | 7/1995 | Mathews ................. | 600/323 |
| 5,437,275 A | 8/1995 | Amundsen et al. | |
| 5,482,034 A * | 1/1996 | Lewis et al. ............ | 600/323 |
| 5,507,752 A * | 4/1996 | Elliott .................... | 606/123 |
| 5,546,955 A | 8/1996 | Wilk | |
| 5,584,296 A * | 12/1996 | Cui et al. ................ | 600/479 |
| 5,638,593 A | 6/1997 | Gerhardt et al. | |
| 5,776,058 A | 7/1998 | Levinson et al. | |
| 5,779,631 A | 7/1998 | Chance | |
| 5,810,724 A | 9/1998 | Gronvall | |
| 5,813,980 A | 9/1998 | Levinson et al. | |
| 5,817,008 A * | 10/1998 | Rafert et al. ............ | 600/323 |
| 5,823,952 A | 10/1998 | Levinson et al. | |
| 5,842,982 A | 12/1998 | Mannheimer | |
| 5,851,179 A | 12/1998 | Ritson et al. | |
| 5,931,789 A * | 8/1999 | Alfano et al. ........... | 600/310 |
| 5,983,129 A | 11/1999 | Cowan et al. | |
| 5,987,351 A | 11/1999 | Chance | |
| 5,995,857 A | 11/1999 | Toomim et al. | |
| 6,456,862 B1 * | 9/2002 | Benni ..................... | 600/331 |
| 6,575,902 B1 | 6/2003 | Burton | |
| 6,577,884 B1 * | 6/2003 | Boas ...................... | 600/310 |
| 6,626,537 B1 * | 9/2003 | Odom et al. ............ | 600/318 |
| 2003/0229276 A1 * | 12/2003 | Sarussi et al. .......... | 600/322 |

FOREIGN PATENT DOCUMENTS

| | | |
|---|---|---|
| DE | 4429845 C1 | 10/1995 |
| GB | 2135074 A | 8/1984 |
| WO | WO 96/15714 | 5/1996 |
| WO | WO 97/20494 | 6/1997 |

* cited by examiner

*Primary Examiner*—Eric F. Winakur
(74) *Attorney, Agent, or Firm*—Fletcher Yoder

(57) ABSTRACT

A method for use and an improved oximeter sensor substrate that is conforming to the shape of the patient's forehead. In one embodiment, the present invention is an oximeter sensor, having a substrate with a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter. In one embodiment, the substrate includes a hat that holds the emitter and the detector in a spaced-part manner against the patient's forehead.

13 Claims, 3 Drawing Sheets

HAT-BASED OXIMETER SENSOR

BACKGROUND OF THE INVENTION

The present invention relates to optical oximeter sensors, and in particular to hat-based pulse oximeter sensors.

Many types of optical sensors are used to measure physiological characteristics of a patient. Typically, an optical sensor provides emitted light which is then scattered through a portion of a patient's tissue and detected. Various characteristics of a patient can be determined from analyzing such light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Certain types of oximeter sensors are applied to a patient's forehead. To aid in the sensor's proper placement and the proper application of pressure by the sensor to the forehead site, some forehead sensors are maintained at the forehead site by either the assistance of an adhesive layer and/or a headband. While these approaches are helpful, there is still a need for an improved and easy way of placing, retaining, and locating the sensor on the forehead of its user.

BRIEF SUMMARY OF THE INVENTION

The present invention provides an oximeter sensor which will attach to a patient's forehead in an improved manner. In certain embodiments, the securing of the sensor to the forehead of the patient is achieved by attaching the sensor to the inside of hat which is worn by the patient when the sensor is in use.

In one embodiment, the present invention is an oximeter sensor, having: a substrate having a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter.

In one embodiment, the substrate is resilient and has a shape conformable to the forehead of a patient.

In one embodiment, the substrate includes an adhesive layer for adhering to the forehead of a patient.

In one embodiment, a hat is used for holding the sensor against the patient's forehead.

In one embodiment, the substrate is adhered to the inside of said hat.

In one embodiment, the substrate is adhesively attached to the inside of the hat. Alternately, the substrate is sewn into the hat.

In another embodiment, the present invention provides a method for determination of a blood characteristic, including: applying an emitter and a detector to spaced-apart positions on a forehead of a patient in the lower forehead region, above the eyebrow, with both the detector and the emitter placed above and predominantly lateral of the iris; securing the emitter and detector to the patient; emitting electromagnetic radiation with the emitter; detecting electromagnetic radiation scattered by the tissues of the forehead by the detector and producing a detector signal; and determining a blood characteristic in the patient from the detector signal.

In one embodiment, the securing of the emitter and the detector to the patient's forehead is achieved by attaching the emitter and the detector to an inside of a hat, and placing the hat on the head of the patient.

For a further understanding of the nature and advantages of the present invention, reference should be made to the following description in conjunction with the accompanying drawings.

DETAILED DESCRIPTION OF THE INVENTION

The embodiments of the present invention are directed towards configuring a reflectance-type oximeter sensor for placement in a hat in order to provide a relatively easy means of placing, retaining, and locating the sensor on the forehead of the user. With regard to the location of the sensor on the patient's forehead, it is preferred to have the sensor be located on the lower forehead region, above the eyebrow, with the sensor optics (emitter and detector) located above and predominantly lateral to or centered over the iris. The oximeter sensor can be attached to the inside band of a hat. The precise location of the reflectance sensor in the hat allows appropriate placement of the sensor in the optimal forehead location by a user not skilled in sensor placement. It has been found that the placement of a reflectance forehead sensor is a factor in the accurate determination of a blood flow characteristic, due to the vasculature of the forehead. In addition, it has been shown that having a certain amount of pressure on the forehead sensor can reduce the incidence of venous pulsations effects on the oximeter reading. The placement of the sensor in the band of the hat would minimize these issues, as the placement of a hat is fairly repeatable and predictable. A hat-based oximeter sensor as embodied by the present invention can be used on patients in clinical settings, or by athletes, soldiers, firemen, or in any environment where information related to a physiological parameter, such as heart rate or oxygen saturation information is desired.

Figure 1:
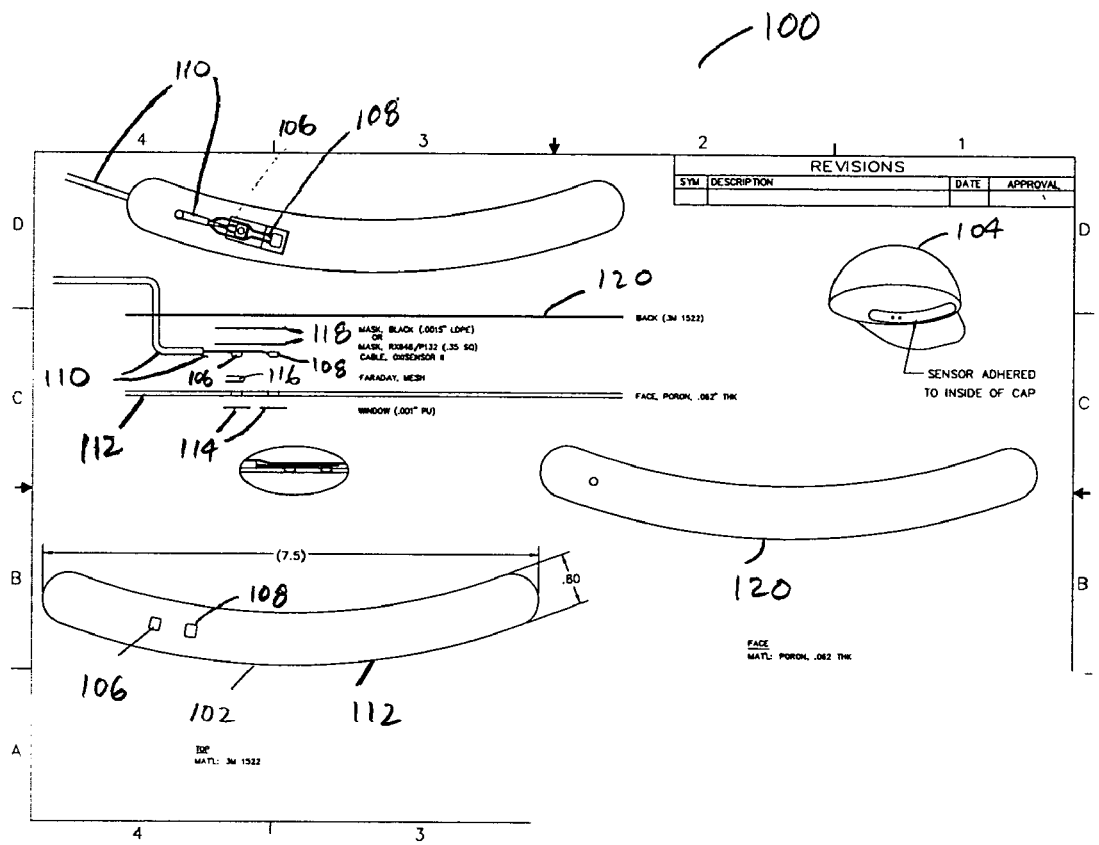
FIG. 1 is an assembly drawing of an embodiment of the sensor in accordance with the present invention that can be placed within a hat or cap.

FIG. 1 is an assembly drawing of an embodiment of the sensor in accordance with the present invention that can be placed within a hat or cap. This figure shows an oximeter sensor placed on a substrate 102 that can be placed or adhered to the inside of a hat 104. In the hat-based embodiment, the sensor uses an emitter 106 containing two discrete wavelengths and a detector 108 placed more than 2 mm away, and ideally 10 mm–15 mm from the emitter. The surface 102 can be black in order to minimize any shunting of light between sensor and patient skin. The sensor in a hat could be used in conjunction with a small, portable oximeter to allow mobility of the user during activities. Similarly, the sensor could be incorporated into a headband. Alternately, it may be desirable to provide a sensor with adhesive backing that would allow the user to place the sensor in a hat of their choice. Also shown in FIG. 1 is a cable 110 for providing drive current to the LED and for providing the detector signal to the oximeter. The cable provides the electrical connection to the monitor; it also provides power for the emitter, signal carrying conductors from the detector, and shielding to protect the small signals from the detector against external electrical interference.

The sensor is shown in a multi-layer structure having a face portion 112. The face 112 is the surface that is placed against the patient's skin. The face material may have an adhesive layer such as an acrylic or synthetic rubber adhesive, or it may be without adhesive, and typically made from a foam PVC or foam polyurethane material. The face 112 component is preferably black so as to minimize the incidence of reflected light that does not go through the tissue. Below the face layer 112 are two windows 114. The windows 114 are generally a clear component, such as for example, a thin film or a clear molded plastic component that makes contact with the skin. The thin film window may be a polyurethane or an acrylic adhesive on a polyester film. The intent of the window 114 is to provide an efficient optical coupling mechanism between the optical components (emitter and detector) and the skin. Located above the face 114, is a Faraday shield 116. The Faraday shield 116 is a conductive material, for example, a copper film or copper mesh, that is electrically connected to the monitor ground to help shield the detector from extraneous electrical interference while passing light to the detector. Next located are the LED 106 and the detector 108. Above the LED and the detector is a mask layer, which may include more than one mask layer. The mask layer 118 is generally a thin film that is intended to block light from entering the back side of the sensor, or from traveling directly from emitter to detector (shunt light). The purpose of the mask 118 is to ensure that all of the light reaching the detector is light from the emitter that has traveled through the capillary bed. Above the mask layer 118 is the back layer 120. The back or the top layer is the non-tissue contacting surface of the sensor. This layer may include a cosmetic finish for the sensor, which can be white with some printed artwork identifying the sensor. Typical materials may be Velcro loop, or soft PVC foam. In a case where the sensor is mounted inside a hat or cap, the top layer is sometimes referred to as the back layer. In this case, the back layer may include a double stick adhesive so that it can be mounted inside the hat.

Figure 2:
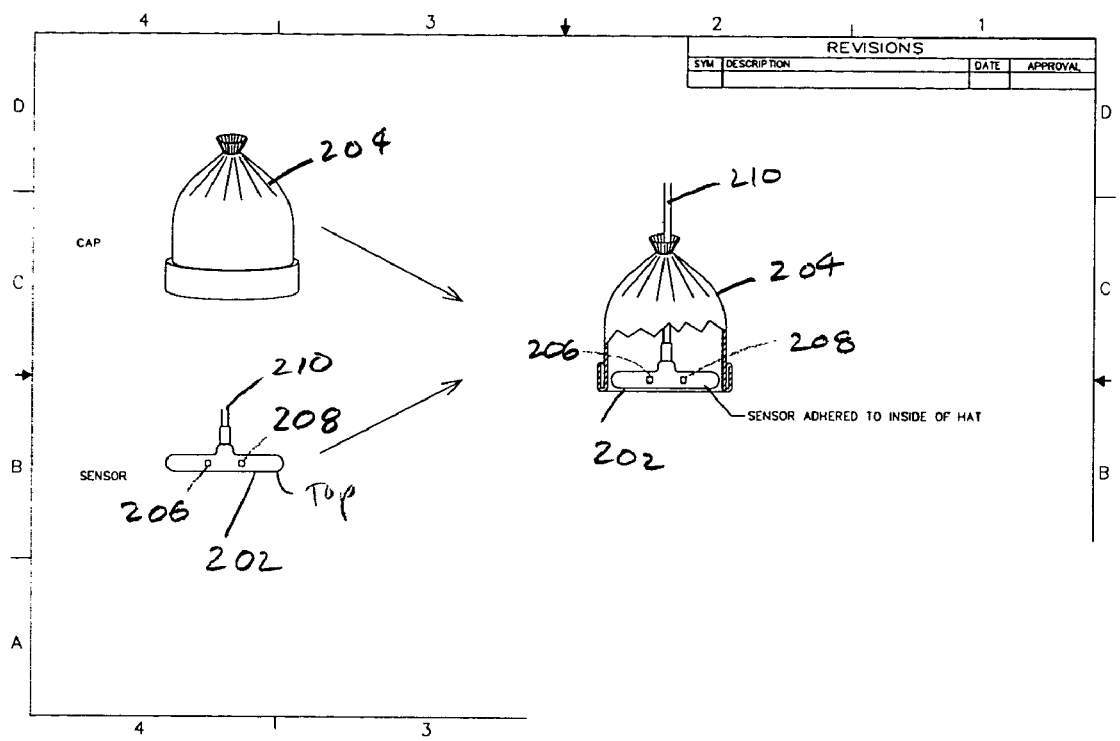
FIG. 2 is a drawing of a stocking hat, with an embodiment of the sensor in accordance with the present invention shown mounted in the hat.

FIG. 2 shows a stocking hat, with an embodiment of the sensor in accordance with the present invention shown mounted in the hat. This alternate embodiment of the present invention, is directed towards the placement of a small reflectance sensor 202 in a stocking cap or beanie 204. FIG. 2 shows the sensor carrier layer 202 holding an LED 206 and a detector 208 and a cable 210, similar to the ones described above in conjunction with FIG. 1. This embodiment may be used for neonates. This embodiment would allow easy placement of a sensor on the forehead of a patient while applying a predictable pressure on the sensor. The sensor in a hat also resolves a concern about the cosmetic appearance of having a sensor on the forehead of the patient. A sensor in a stocking cap is much more acceptable to a parent than having a sensor located on the forehead. Depending on the tension of the stocking cap, provided by its own stretchiness or by an adjustable integral headband strap, the sensor may have a light tack adhesive, or no adhesive at all. The lack of an adhesive layer is a desirable feature, especially on neonates as adhesives may sometimes leave visible damage to the fragile skin of a neonate.

Figure 3:
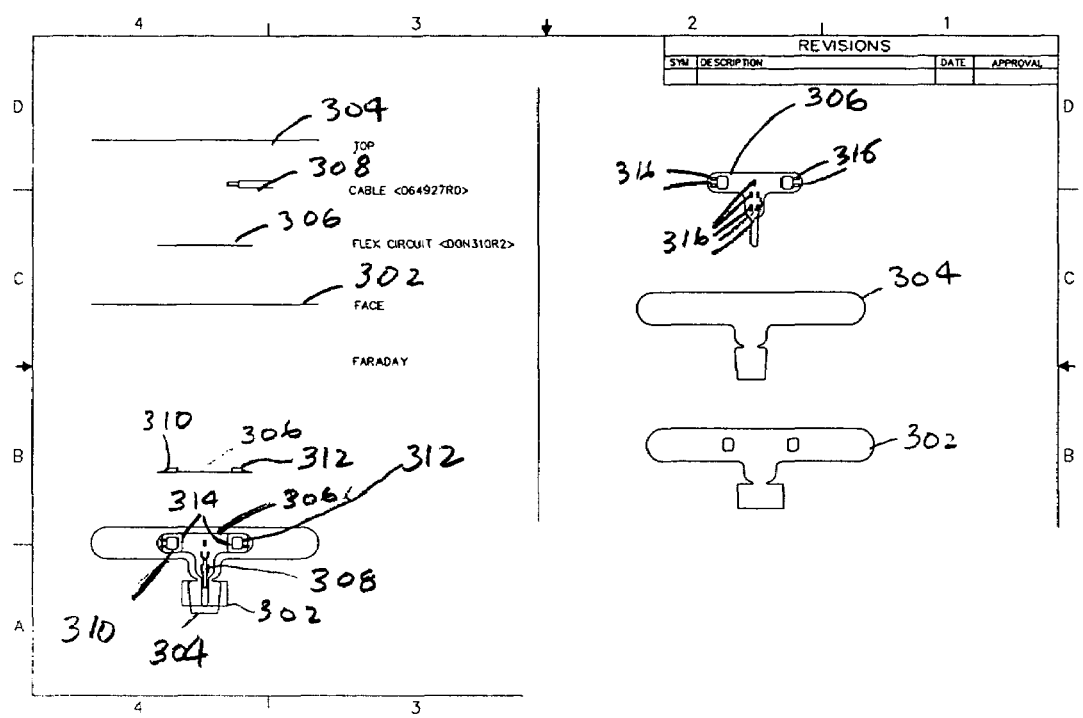
FIG. 3 is an assembly drawing of an embodiment of the sensor of FIG. 1 or 2.

FIG. 3 is an assembly drawing for an embodiment of the sensor of FIG. 1 or 2. FIG. 3 shows that the sensor portion generally includes a face layer 302, a top layer 304 and a flex circuit 306 that is placed between the face and top layers. Also shown in FIG. 3 is a multi-layer unassembled view showing the relative positions of the face 302, flex circuit 306, a cable 308 and the top layer 304. The flex circuit layer 306 holds the emitter (LED) 310 and the detector 312 as well as the mask layer 314 and Faraday shield as described above. The flex circuit 306 also has several holes 316 to allow for electrical connections between the leads in the cable and the LED and the detector.

As will be understood by those skilled in the art, the present invention may be embodied in other specific forms without departing from the essential characteristics thereof. For example, the sensor may include adhesive layers for adhering to the inside of a hat or the user's skin, or that that the sensor may be sewn into the hat. These other embodiments are intended to be included within the scope of the present invention, which is set forth in the following claims.

What is claimed is:

1. A pulse oximetry sensor comprising:
   a stocking cap;
   a substrate disposed on the stocking cap;
   an emitter disposed on the substrate;
   a detector disposed on the substrate; and
   a cable disposed on the substrate, wherein the cable extends from the substrate at an angle not in-line with an imaginary axis extending through the emitter and the detector, and wherein the cable extends through an open portion of the stocking cap configured to be proximate to a top of the stocking cap when the stocking cap is applied to the patient.

2. The sensor of claim 1, wherein the cable is disposed on the substrate in a substantially orthogonal direction relative to the axis.

3. The sensor of claim 1, wherein the cable is disposed on the substrate such that the cable substantially bisects the emitter and the detector.

4. The sensor of claim 3, wherein the substrate comprises a T-shape.

5. The sensor of claim 1, wherein the sensor is adapted to operate in a reflectance mode.

6. The sensor of claim 1, wherein the substrate is adapted to be used on a patient's forehead.

7. The sensor of claim 1, wherein the stocking cap comprises a neonatal stocking cap.

8. The sensor of claim 1, wherein the substrate comprises an adhesive layer adapted to attach the substrate to the headcovering.

9. A headcovering comprising:
   a neonatal stocking cap; and
   a pulse oximetry sensor, wherein the pulse oximetry sensor comprises:
      a substrate;
      an emitter disposed on the substrate;
      a detector disposed on the substrate; and
      a cable disposed on the substrate, wherein the cable extends from the substrate through an open portion of the neonatal stocking cap configured to be proximate to a top of the neonatal stocking cap when the neonatal stocking cap is applied to the patient.

10. The sensor of claim 9, wherein the substrate is conformable to a forehead-contacting surface of the headcovering.

11. The sensor of claim 9, wherein the substrate is adapted to be attached to the headcovering.

12. The sensor of claim 9, wherein the substrate comprises an adhesive layer adapted to attach the substrate to the headcovering.

13. The sensor of claim 9, wherein the cable is secured by a portion of the neonatal stocking cap.

* * * * *